United States Patent [19]

Soules

[11] Patent Number: 5,610,515

[45] Date of Patent: Mar. 11, 1997

[54] EDDY CURRENT TEST METHOD FOR RESIDUAL STRESS IN NON-FERROMAGNETIC METAL OBJECTS

[75] Inventor: Jack A. Soules, Shaker Heights, Ohio

[73] Assignee: Cleveland State University, Cleveland, Ohio

[21] Appl. No.: 540,496

[22] Filed: Oct. 10, 1995

[51] Int. Cl.[6] .................... G01B 7/24; G01N 27/90; G01R 33/12
[52] U.S. Cl. .................... 324/209; 324/225; 324/238
[58] Field of Search .................... 324/209, 225, 324/234, 238; 73/779

[56] References Cited

U.S. PATENT DOCUMENTS

| | | | |
|---|---|---|---|
| 4,528,856 | 7/1985 | Junker et al. | 324/209 X |
| 4,706,020 | 11/1987 | Viertl et al. | 324/238 |
| 4,893,079 | 1/1990 | Kustra et al. | 324/234 |
| 5,055,784 | 10/1991 | Jaeger et al. | 324/234 X |
| 5,184,071 | 2/1993 | Tasca | 324/238 |

*Primary Examiner*—Gerard R. Strecker
*Attorney, Agent, or Firm*—John F. McDevitt

[57] ABSTRACT

A novel test method enabling residual stress in non-ferromagnetic metal objects to be reliably measured which requires particular circuit elements in the alternating current bridge circuit being employed for measurement to be environmentally controlled. In doing so, the selected circuit resistor elements are thermally isolated in a manner enabling lift-off impedance values to non-destructively measure near-surface residual stress in the metal object being tested.

11 Claims, No Drawings

EDDY CURRENT TEST METHOD FOR RESIDUAL STRESS IN NON-FERROMAGNETIC METAL OBJECTS

BACKGROUND OF THE INVENTION

This invention relates generally to a test method for determining residual stress in non-ferromagnetic metal objects and more particularly to a novel eddy current measurement procedure enabling extremely minor conductivity changes in such metal objects to now be reliably measured.

As a non-destructive test procedure, eddy current measurement has long been employed for detection of relatively macroscopic defects or compositional variations in non-ferromagnetic metal objects such as surface and sub-surface cracks or flaws, irregularities in material structure and still other variations in metallurgical characteristics. Various commercially available testing equipment is employed for such measurements to include automatically controlled measurement means such as the smart Eddy™ system, manufactured by FaAA Products Corporation, Menlo Park, Calif., which utilizes software programmed general purpose computer means operatively associated with an alternating current bridge measuring circuit. The commercially available test equipment does not reliably detect much smaller conductivity changes resulting from residual stress in these metal objects, however, thereby requiring still other means for measurement of these important physical characteristics. To further explain, residual stress in titanium and aluminum alloys such as near surface compression or tension resulting from mechanical action such as shot-peening or rolling has not thus far been reliably detected with the commercially available test equipment. Thus, a customary displacement or lift-off measurement procedure employed with the commercially available test equipment does not produce accurate impedance level changes indicative of the residual stress condition existing in the metal object being tested. It remains desirable, therefore, to find an alternate test procedure whereby extremely small impedance level differences attributable to the existing stress condition in the tested metal object is reliably detected.

Accordingly, it is an important object of the present invention, therefore, to provide an extremely sensitive eddy current test procedure for measurement of residual stress in non-ferromagnetic metal objects.

It is another important object of the present invention to modify conventional eddy current test equipment in a manner enabling accurate detection of the existing residual stress condition in non-ferromagnetic metal objects.

It is a still further important object of the present invention to significantly increase the detection sensitivity of conventional eddy current test equipment in a simplified manner not requiring extensive modification of its component parts.

These and further important objects of the present invention will become more apparent upon considering the following detailed description of the present invention.

SUMMARY OF THE INVENTION

It has now been discovered, surprisingly, that extremely sensitive detection of the existing stress condition in non-ferromagnetic metal objects has been provided by exercising particular environmental controls during the test procedure. Basically, critical circuit elements in an otherwise conventional alternating current bridge circuit being employed are now operated in a particular manner so as to become relatively insensitive to environmental fluctuations experienced during the measurement. To carry out the present test method for determining residual stress entails (a) contacting the surface of said non-ferromagnetic metal object being tested with a probe device having spaced apart identical test and comparison induction coils suitable for operation in the frequency range from about 100 KHz to about 10 MHz, the test coil in said probe device being placed adjacent the contacted surface, (b) the test and comparison induction coils of said probe device providing bridge arms in an alternating current bridge circuit formed in combination with resistor elements, said resistor elements exhibiting the same resistance characteristics including a relatively low thermal coefficient value, and with all resistor elements in said bridge circuit being physically maintained together for operation in a temperature range where resistance change with temperature change is minimal, (c) energizing said bridge circuit in an operating frequency in the range from about 100 KHz up to about 10 MHz causing self-inductance eddy current flow in both induction coils of said probe while remaining in contact with the surface of said non-ferromagnetic metal object, (d) balancing the bridge circuit during said operating conditions, (e) displacing the probe device from the surface of said non-ferromagnetic object while still maintaining the bridge circuit at the same operating conditions to determine any impedance change attributable thereto, (f) repeating steps (a) thru (e) with the probe device at the same operating conditions while employing a relatively stress free non-ferromagnetic metal object having the same metallurgical characteristics as the already tested non-ferromagnetic metal object, and (g) comparing the impedance change obtained upon probe displacement for the individual non-ferromagnetic objects for any difference found therebetween, such difference determining the amount of residual stress existing in the non-ferromagnetic metal object being tested. Conducting such test procedure in the foregoing manner has been found to increase measurement sensitivity by a factor of ten or more with the impedance value change being detected to an accuracy of at least five parts per million.

Proper operation of the commercially supplied alternating current bridge circuit in the above identified smart Eddy™ test equipment for conformity with the above test procedure required but a relatively simple modification. More particularly, the four principal 50 ohm resistor elements incorporated in the supplied Detector Board Bridge Input and Amplifier component of said test equipment were physically removed for replacement and relocation. In so doing, resistor elements were substituted having the same resistance value but which exhibited relatively little resistance change over a range of about 20° C. from a nominal 35° C. measurement temperature. As an additional modification, the substituted resistor elements were physically joined together with conventional synthetic polymer adhesive thereby reducing sensitivity of the modified bridge measuring circuit to thermal fluctuations. Optional physical clamping of the supplied probe device in the illustrated test equipment provided further vibration isolation during measurement to be achieved such that the modified bridge circuitry could now be balanced and remain balanced to within one or two parts per million of impedance change over time periods of one minute or more for the first time. As a result, titanium alloy samples subjected to shot-peening treatment were tested and found to exhibit near surface residual stress in the order of ten to one hundred parts per million.

Probe devices suitable for conducting the present test procedure can be furnished by the above named test equipment manufacturer in the designated operating frequency range. In general, such probe device employs a pair of spaced apart test and comparison induction coils entirely sealed within an electrically non-conductive jacket, said test coil being sufficiently adjacent to the jacket wall so to induce eddy current flow in the non-ferromagnetic metal object being tested upon probe placement in physical contact therewith while said comparison coil is positioned remote therefrom and with said test and comparison coils being electrically interconnected to serve as bridge arm components in the alternating current bridge circuit further electrically connected to said probe device. Electrical connection of said probe device to the alternating bridge circuit also generally employs individual conductor elements connected to each induction coil in combination with a common conductor element connecting both induction coils. The electrically non-conductive jacket for said probe device can be formed with conventional synthetic organic polymer materials.

DETAILED DESCRIPTION OF THE PREFERRED EMBODIMENTS

A shot-peened titanium based alloy containing approximately six weight per cent aluminum and four weight vanadium was non-destructively measured in accordance with the above defined method to determine near surface residual stress in the top surface region extending about 0.3 millimeters in depth. The test procedure was conducted on small samples having approximately 0.2 cubic millimeters volume employing a commercial smart Eddy™ 3.0 test equipment which had been modified as further above defined. This test equipment consisted of the host computer, the associated software, the instrument circuit module including the aforementioned bridge measuring circuit and furnished test probes designed for high frequency operation in the range 2 MHz to 10 MHz. In accordance with the present test procedure, increasing measurement sensitivity first entailed equipment modification in the previously defined manner to include replacement and relocation of the 50 ohm bridge arm resistor elements in the furnished circuit module together with isolating the so modified equipment from mechanical vibration. The four bridge arm resistor elements selected for replacement had approximately five parts per million temperature coefficients. Prior to such modification, temperatures of the probe, test sample and bridge measuring circuitry were observed to fluctuate over a range of about 6° C. which resulted in apparent random surface impedance fluctuations, some ten times those ultimately measured after the above defined equipment modification.

The particular measurement procedure conducted with the above modified test equipment entailed lifting the probe device from the sample being tested to generate the customary lift-off curve. This equipment enables the axes of the impedance curve to be rotated and expanded on the computer display screen with only changes in the probe impedance being displayed as percentage values (100 $\Delta Z/Z$). With such procedure, it now becomes possible to detect impedance change attributable to shot peening in the samples being tested to a typical level as small as 0.006 percent. On the other hand, samples having a shot peening depth less than a nominal 0.25 millimeter could not be reliably measured with the tests conducted.

The titanium alloy samples tested in the foregoing manner for residual stress attributable to shot peening were sections of hot rolled sheet measuring 100×105×12.7 millimeters in size. Each sample was shot peened over two thirds of its surface area with the center one third section being covered with tape to protect the covered area from shot peening action. A series of test measurements on these samples was conducted with a test probe designed for 5 MHz driving frequency at operating frequencies of 2 MHz, 7 MHz and 10 MHz. Prior to measurement the test samples were also carefully polished over a partial surface section to determine any possible effects of surface distortion caused by the shot peening process. Said test measurements were further conducted at nominal measurement temperatures of approximately 35° C. so as to be maintained within the approximately 20° C. temperature range where resistance change of the replacement resistor elements remains minimal. The relatively minute impedance changes due to shot peening induced compressive stress in the tested samples are reported in the Table below.

TABLE

| Sample | Fractional Impedance Change ($\Delta Z/Z \times 10^{-6}$) | | |
|---|---|---|---|
| | 2 MHz | 7 MHz | 10 MHz |
| #1 (unpolished sample) | 70 | 130 | 130 |
| #1 (polished sample) | 60 | 120 | 90 |
| #2 (unpolished sample) | — | 145 | — |
| #3 (unpolished sample) | 20 | 50 | 30 |
| #3 (polished sample) | 50 | 40 | 40 |
| #4 (unpolished sample) | 50 | 70 | 40 |
| #4 (polished sample) | 80 | 60 | 70 |

It is first apparent from the above test measurements that irregularities in the shot peened surface produces only insignificant variation in the impedance changes resulting from the shot peening action. It is further evident from said measurements that shot peening causes higher impedance in the near surface region of the samples in every case. It follows therefrom that such decrease in conductivity induced in non-ferromagnetic metals can now be accurately measured in accordance with the herein improved measurement procedure.

It will be apparent from the foregoing description that a broadly useful and novel non-destructive test method for determining residual stress in non-ferromagnetic metal objects has been provided now enabling extremely sensitive measurement of minute near surface stress values. It is contemplated that such measurement procedure can be employed for a broad range of non-ferromagnetic metal materials other than specifically illustrated herein, however, to include measurement of residual stress resulting from applied mechanical forces other than shot peening or rolling. Likewise, it is contemplated that the herein disclosed test procedure can be carried out with other test equipment employing alternating current bridge measuring circuitry means than herein illustrated, such as various manually operated forms of such test equipment. Consequently, it is intended to limit the present invention only by the scope of the appended claims.

What I claim as new and desire to secure by letters Patent of the United States is:

1. A test method to determine residual stress in a non-ferromagnetic metal object which comprises:

(a) contacting the surface of said non-ferromagnetic metal object with a probe device having spaced apart identical test and comparison induction coils suitable for operation in the frequency range from 100 KHz up to about 10 MHz, the probe device being constructed so that only the test induction coil in said probe device physically contacts the surface of the non-ferromagnetic metal object being tested while the comparison induction coil in said probe device remains physically positioned remote therefrom, (b) the test and comparison induction coils of said probe device providing bridge arms in an alternating current bridge circuit formed in combination with resistor elements exhibiting the same resistance characteristics including a relatively low thermal coefficient value, and with all resistor elements in said bridge circuit being kept isolated at a remote physical location enabling operation in a temperature range varying no more than about 20° C. from the temperature at which the resistance value for the resistor elements is minimum, (c) energizing the bridge circuit at an operating frequency in the range from about 100 KHz up to about 10 MHz causing self-inductance eddy current flow in both induction coils of said probe device while the test coil in said probe device remains in contact with the surface of said non-ferromagnetic metal object, (d) balancing the bridge circuit during said operating conditions so as to remain balanced to within less than two parts per million of impedance change over a time period of at least one minute, (e) displacing the probe device from the surface of said non-ferromagnetic metal object while still maintaining the bridge circuit at the same operating conditions to determine the impedance change attributable thereto, (f) repeating steps (a) thru (e) with the probe device at the same operating conditions while employing a relatively stress free non-ferromagnetic metal object having the same metallurgical characteristics as the already tested non-ferromagnetic metal object, and (g) comparing the impedance change obtained upon probe displacement for the individual non-ferromagnetic metal objects for any difference found there-between to an accuracy of at least five parts per million, said difference determining the amount of residual stress existing in the non-ferromagnetic metal object being tested.

2. The method of claim 1 whereby residual stress existing primarily in the near surface region of a non-ferromagnetic metal object is detected.

3. The method of claim 2 whereby the residual surface stress in a non-ferromagnetic metal object after shot peening is detected.

4. The method of claim 2 whereby the residual surface stress in a non-ferromagnetic metal object after mechanical rolling is detected.

5. The method of claim 1 whereby the residual stress in a non-ferromagnetic metal object fabricated with titanium alloy is detected.

6. The method of claim 1 whereby the operating frequency determines the depth in a non-ferromagnetic metal object to which residual stress is detected.

7. The method of claim 1 whereby the size and shape of the coil probe determine proper operation in the specified frequency range.

8. The method of claim 1 wherein all resistor elements in the alternating current bridge measuring circuit are physically joined together.

9. The method of claim 8 wherein said resistor elements are physically joined together with an electrically non-conductive adhesive.

10. The method of claim 1 wherein said detection of residual stress is carried out automatically utilizing programmed computer means operatively associated with the alternating current bridge measuring circuit.

11. The method of claim 10 wherein isolation from mechanical vibration is also provided.

* * * * *